United States Patent [19]

Smith

[11] 4,189,834
[45] Feb. 26, 1980

[54] DENTAL REINFORCING PINS

[76] Inventor: Andrew J. Smith, 3 Leighton Crescent, London N.W. 5, England

[21] Appl. No.: 804,831

[22] Filed: Jun. 8, 1977

Related U.S. Application Data

[63] Continuation of Ser. No. 639,095, Dec. 9, 1975, abandoned.

[51] Int. Cl.² .............................................. A61K 5/02
[52] U.S. Cl. .................................................... 433/225
[58] Field of Search ....................... 32/11, 7, 15; 85/61, 85/41

[56] References Cited

U.S. PATENT DOCUMENTS

| | | | |
|---|---|---|---|
| 2,289,785 | 7/1942 | Hutchinson, Jr. | 85/41 |
| 2,310,409 | 2/1943 | Ellman | 32/58 |
| 3,576,073 | 4/1971 | Weissman | 32/15 |
| 3,675,328 | 7/1972 | Wellsman | 32/15 |
| 3,675,329 | 7/1972 | Weissman | 32/15 |
| 3,861,043 | 1/1975 | Lieb et al. | 32/15 |
| 3,875,665 | 4/1974 | Weissman | 32/15 |
| 3,932,939 | 1/1976 | Weissman | 32/2 |

Primary Examiner—Robert Peshock
Attorney, Agent, or Firm—Beveridge, DeGrandi, Kline & Lunsford

[57] ABSTRACT

A dental reinforcing pin including a threaded portion, for self-tapping insertion in a bore formed in a tooth understructure, and a connecting portion formed integrally with the threaded portion. The connecting portion includes a shank, adapted for engagement in a dental handpiece, and a weakened portion intermediate the threaded portion and the connecting portion to permit shearing and separation of the connecting portion from the threaded portion when the pin is inserted to the depth of the bore.

5 Claims, 3 Drawing Figures

DENTAL REINFORCING PINS

This is a continuation of application Ser. No. 639,095 filed Dec. 9, 1975 now abandoned.

The invention relates to a dental reinforcing pin for use in the anchoring of a superstructure to a tooth understructure.

According to the invention, there is provided a dental reinforcing pin comprising a threaded portion for self-tapping insertion in a bore formed in a tooth understructure and a connecting portion formed integrally with the threaded portion, the connecting portion including a shank capable of slidable insertion in a dental hand-piece, and including a weakened portion intermediate the threaded portion and the connecting portion to permit shearing and separation of the connecting portion from the threaded portion.

Figure 1:
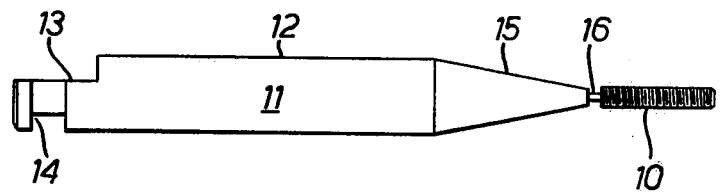
Figure 2:
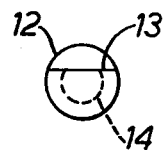
Figure 3:
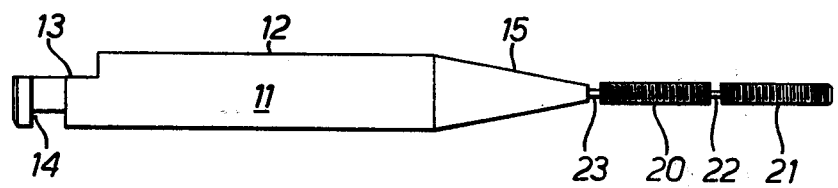

For a better understanding of the invention, examples thereof will now be described with reference to the accompanying drawings, in which;

FIG. 1 is a side elevation of a dental reinforcing pin machined from stainless steel wire, FIG. 2 is a end elevation of the dental reinforcing pin and FIG. 3 is a side elevation of another embodiment of the dental pin.

Referring now to FIGS. 1 and 2, the dental reinforcing pin has a screw-threaded portion 10 at one end thereof. The threaded portion 10 may have an outside diameter of 0.76 mm and a length of 4 mm. Formed integrally with the threaded portion 10 is a connecting portion 11 comprising an elongated circular-cylindrical shank 12. The diameter of the shank 12 is larger than that of the threaded portion 10 and is such that the shank will be an easy sliding fit in a standard dental hand-piece. The shank 12 is shaped at its free end, providing a segmental cut-away portion 13 and part-annular groove 14 so that the shank 12 can co-operate with the latch mechanism of a latching-type dental hand-piece and be locked thereby. The end of the connecting portion 11 adjacent the threaded portion 10 is constituted by a frusto-conical portion 15. Intermediate the threaded portion 10 and the connecting portion 11 is a reduced diameter portion or neck 16 having a diameter less than the root diameter of the threaded portion 10 so as to provide a fracture or shear portion.

In operation, carious matter is removed from the surface of a broken-down tooth leaving a sound dentine understructure. A hole is drilled in the denture in well-known manner with a dental drill. The reinforcing pin is loaded in a latching-type contra-angle dental hand-piece by sliding the shank 12 into the hand-piece and locking it with the latch on the hand-piece. The threaded portion 10 and the frusto-conical portion 15 now project clear of the barrel of the hand-piece. The hand-piece drive, comprising an air motor or other known means, is now operated, causing rotation of the dental pin. The reinforcing pin is now aligned and engaged with the drilled hole, the frusto-conical portion 15 aiding visibility. The reinforcing pin will now advance in self-tapping self-threading manner in the drilled hole which has a diameter slightly less than the threaded diameter so that a good anchorage is obtained by the inter-engagement of the thread on the pin and the thread formed in the dentine. When the pin has penetrated to the bottom or nearly the bottom of the hole so that resistance is met to further movement, the neck 16 automatically shears so that the connecting portion 12 is separated from the threaded portion 10. The depth of the drilled hole can be chosen so that when the shear-off point is reached, for example half the length of the threaded portion 10 extends into the dentine and the remainder projects from the tooth understructure. The connecting portion 11 can now be released from the hand-piece and discarded. Finally, the tooth is built up with an amalgam or composite superstructure around the threaded portion in known manner.

It will be apparent that the reinforcing pin described above is very safe in use in that the pin is securely locked to the hand-piece during the insertion and thus the danger of the pin falling into the patient's mouth is minimised. Furthermore, the described pin enables the operation of inserting a threaded portion in a tooth to be performed quickly and easily.

Referring to FIG. 3, a threaded portion comprises two equal sections 20 and 21 joined by a neck 22. A neck 23 is provided intermediate the threaded section 20 and the connecting portion 11. The neck 22 has a slightly smaller diameter than that of the neck 23. The reinforcing pin is operated in the same manner as the first described embodiment except that shear will first occur at the relatively smaller diameter neck 22 so that the connecting portion 11 together with the threaded section 20 separate from the threaded section 21. The hand-piece holding securely the threaded section 20 can now be aligned with a second drilled hole in a tooth. Operation of the hand-piece now causes self-threading insertion of the pin in the second hole and when the pin reaches the bottom of the hole, shear occurs at the neck 23 so that the connecting portion 11 separates from the threaded section 20. By this means, threaded portions can be inserted in two drilled holes without the need to re-load the hand-piece.

In another embodiment of the invention, part of the connecting portion remote from the threaded portion is formed from a material different from that of the threaded portion and is moulded to the remainder of the pin to form an integral structure.

The free end of the connecting portion may be shaped in a different way from that described above to co-operate with locking means on the hand-piece so that the dental pin is locked to the hand-piece.

What I claim is:

1. A dental anchoring device comprising a threaded portion for self-threading insertion in a bore formed in a tooth dentine, a connecting portion forming an integral unit with said threaded portion and having an elongated shank adapted for direct positive attachment in a powered dental hand-piece, and a weakened portion intermediate the threaded portion and one end of the connecting portion for permitting shearing and separation of the connecting portion from the threaded portion; the free end of the connecting portion having a flat portion and a part annular groove, whereby the connecting portion can be latched in a latching-type dental hand-piece to securely retain the dental anchoring device in the hand-piece without dropping therefrom and when said threaded portion is fully inserted in a bore said weakened portion shears to separate said connecting portion from said threaded portion.

2. A dental reinforcing pin, according to claim 1, in which the weakened portion is a neck of smaller diameter than the root diameter of the threaded portion.

3. A dental reinforcing pin according to claim 2, in which the threaded portion is in two sections joined by a further neck, the diameter of the further neck being less than the diameter of the first-mentioned neck whereby shear will tend to occur first at the further neck.

4. A dental anchoring device according to claim 1, in which the shank has a circular cross-section substantially throughout its length.

5. A dental anchoring device as claimed in claim 1 in which the threaded portion and the connecting portion are formed as a single homogeneous piece.

* * * * *

REEXAMINATION CERTIFICATE (260th)
United States Patent [19]

Smith

[11] B1 4,189,834

[45] Certificate Issued Oct. 9, 1984

[54] DENTAL REINFORCING PINS

[75] Inventor: Andrew J. Smith, London, England

[73] Assignee: Fairfax Dental Ltd., Dublin, Ireland

Reexamination Request:
No. 90/000,478, Dec. 9, 1983

Reexamination Certificate for:
Patent No.: 4,189,834
Issued: Feb. 26, 1980
Appl. No.: 804,831
Filed: Jun. 8, 1977

Related U.S. Application Data

[63] Continuation of Ser. No. 639,095, Dec. 9, 1975, abandoned.

[51] Int. Cl.³ .............................................. A61C 3/04
[52] U.S. Cl. ................................................... 433/225
[58] Field of Search ...................... 433/225, 165, 226

[56] References Cited
U.S. PATENT DOCUMENTS 3,576,076  4/1971  Weissman .......................... 433/165
3,726,014  4/1973  Weissman .......................... 433/165

OTHER PUBLICATIONS

"Pin Pointers III Self-threading Pins" by Gerard L. Courtado, Journal Prosthetic Dentistry, 1968, 20 (4) pp. 335–338.
"Conservation of Teeth" by Eccles & Green, pp. 52–53, published 1973.

*Primary Examiner*—Robert Peshock

[57] ABSTRACT

A dental reinforcing pin including a threaded portion, for self-tapping insertion in a bore formed in a tooth understructure, and a connecting portion formed integrally with the threaded portion. The connecting portion includes a shank, adapted for engagement in a dental handpiece, and a weakened portion intermediate the threaded portion and the connecting portion to permit shearing and separation of the connecting portion from the threaded portion when the pin is inserted to the depth of the bore.

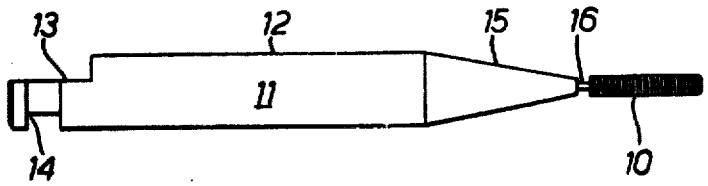

REEXAMINATION CERTIFICATE ISSUED UNDER 35 U.S.C. 307.

NO AMENDMENTS HAVE BEEN MADE TO THE PATENT.

AS A RESULT OF REEXAMINATION, IT HAS BEEN DETERMINED THAT:

The patentability of claims 1-5 is confirmed.

* * * * *

REEXAMINATION CERTIFICATE (1339th)
United States Patent [19]
Smith

[11] B2 4,189,834
[45] Certificate Issued Aug. 21, 1990

[54] DENTAL REINFORCING PINS

[75] Inventor: Andrew J. Smith, London, England

[73] Assignee: Fairfax Dental Ltd, Dublin, Ireland

Reexamination Request:
No. 90/001,299, Aug. 3, 1987

Reexamination Certificate for:
Patent No.: 4,189,834
Issued: Feb. 26, 1980
Appl. No.: 804,831
Filed: Jun. 8, 1977

Reexamination Certificate B1 4,189,834 issued Oct. 9, 1984.

[51] Int. Cl.⁵ .............................................. A61C 5/04
[52] U.S. Cl. .................................................... 433/225
[58] Field of Search ......................................... 433/225

[56] References Cited

U.S. PATENT DOCUMENTS

| | | | |
|---|---|---|---|
| 3,675,328 | 7/1972 | Weissman | 32/15 |
| 3,675,329 | 7/1972 | Weissman | 32/15 |
| 3,861,043 | 1/1975 | Lieb | 32/15 |

FOREIGN PATENT DOCUMENTS 2163953  7/1973  France .

OTHER PUBLICATIONS

"Operative Dental Surgery"–Parfitt and Herbert–7th Edition, 1955, p. 227.
"Pin Pointers. III. Self–Threading Pins"–Gerard L. Courtade–Journal Prosthetic Dentistry, 1968, 20(4), pp. 335–338.

*Primary Examiner*—John J. Wilson

[57] ABSTRACT

A dental reinforcing pin including a threaded portion, for self-tapping insertion in a bore formed in a tooth understructure, and a connecting portion formed integrally with the threaded portion. The connecting portion includes a shank, adapted for engagement in a dental handpiece, and a weakened portion intermediate the threaded portion and the connecting portion to permit shearing and separation of the connecting portion from the threaded portion when the pin is inserted to the depth of the bore.

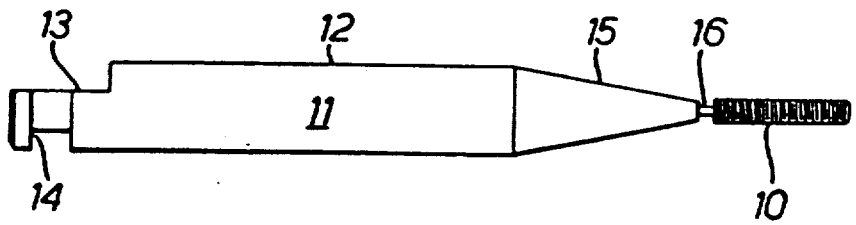

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-5 is confirmed.

* * * * *